US008517922B2

(12) United States Patent
Koitabashi et al.

(10) Patent No.: US 8,517,922 B2
(45) Date of Patent: Aug. 27, 2013

(54) ENDOSCOPE AND ENDOSCOPE SYSTEM

(75) Inventors: Masanobu Koitabashi, Tokyo (JP); Mitsuhiro Ito, Tokyo (JP); Yasukazu Kogen, Tokyo (JP)

(73) Assignee: Olympus Corporation (JP)

( * ) Notice: Subject to any disclaimer, the term of this patent is extended or adjusted under 35 U.S.C. 154(b) by 1262 days.

(21) Appl. No.: 11/564,547

(22) Filed: Nov. 29, 2006

(65) Prior Publication Data

US 2007/0088198 A1     Apr. 19, 2007

(51) Int. Cl.
*A61B 1/00* (2006.01)
*A61B 1/04* (2006.01)
*A61B 1/06* (2006.01)

(52) U.S. Cl.
USPC ............ 600/136; 600/131; 600/175; 600/182

(58) Field of Classification Search
USPC ................. 600/112, 132, 136, 172, 174, 137, 600/176; 385/117
See application file for complete search history.

(56) References Cited

U.S. PATENT DOCUMENTS

| | | | |
|---|---|---|---|
| 4,356,534 A | | 10/1982 | Hattori |
| 4,369,767 A | * | 1/1983 | Shishido ...................... 600/112 |
| 4,433,675 A | | 2/1984 | Konoshima |
| 4,624,243 A | * | 11/1986 | Lowery et al. ............... 600/136 |
| 4,812,007 A | | 3/1989 | Lukas |
| 4,941,457 A | * | 7/1990 | Hasegawa .................... 600/142 |
| 5,193,135 A | * | 3/1993 | Miyagi ......................... 385/117 |
| 5,930,424 A | | 7/1999 | Heimberger et al. |
| 6,004,263 A | * | 12/1999 | Nakaichi et al. ............. 600/176 |
| 6,494,826 B1 | * | 12/2002 | Chatenever et al. .......... 600/112 |

FOREIGN PATENT DOCUMENTS

| | | |
|---|---|---|
| DE | 19729978 A1 | 1/1999 |
| EP | 0 663 602 | 7/1995 |
| EP | 1 091 224 | 4/2001 |
| GB | 2153102 A | 8/1985 |
| JP | 56-60526 | 5/1981 |
| JP | 57-164031 | 10/1982 |
| JP | S59-181410 | 12/1984 |
| JP | 60-161308 | 10/1985 |

(Continued)

OTHER PUBLICATIONS

Office Action issued by Japanese Patent Office on May 6, 2010 in connection with corresponding Japanese application No. 2004-358466 and English translation thereof.

(Continued)

*Primary Examiner* — Alireza Nia
(74) *Attorney, Agent, or Firm* — Ostrolenk Faber LLP (57) ABSTRACT

A socket section 72 for providing a first light guide 13 is supported movably in an endoscope main body 4, and a plug section 62 for fixing a second light guide 15 is disposed in an endoscope insertion section 5. The socket section 72 is configured to move freely in an insertion direction of the endoscope insertion section 5 and to a direction orthogonal with respect to the insertion direction. Furthermore, an attachment-detachment-detecting switch 33 is disposed in the endoscope main body 4 so as to detect that the endoscope insertion section 5 has been separated from the endoscope main body 4 before the plug section 62 is freely detached from the socket section 72. By this configuration, it is possible to attach the endoscope insertion section from the endoscope main body and detach them easily and reliably, in particular, to reduce loss of light caused by the attachment and the detachment.

6 Claims, 4 Drawing Sheets

(56) References Cited

FOREIGN PATENT DOCUMENTS

| JP | 03-275030 | 12/1991 |
|----|-----------|---------|
| JP | 05-027184 | 2/1993 |
| JP | 05-220109 | 8/1993 |
| JP | 06-254049 | 9/1994 |
| JP | 07-072353 | 3/1995 |
| JP | 08-211308 | 8/1996 |
| JP | 10-201710 | 8/1998 |
| JP | 10-227945 | 8/1998 |
| JP | 10-295640 | 11/1998 |
| JP | 11-197105 | 7/1999 |
| JP | 2000-014626 | 1/2000 |
| JP | 2000-079091 | 3/2000 |
| JP | 2001-161629 | 6/2001 |
| JP | 2001-321338 | 11/2001 |
| JP | 2002-177216 | 6/2002 |

OTHER PUBLICATIONS

Office Action issued by Japanese Patent Office on Nov. 24, 2010 in connection with corresponding Japanese application No. 2004-358466 and English translation thereof.

\* cited by examiner

ENDOSCOPE AND ENDOSCOPE SYSTEM

The present application is based on patent application No. 2004-358466 filed in Japan on Dec. 10, 2004, the content of which is incorporated herein by reference.

BACKGROUND OF THE INVENTION

1. Field of the Invention

The present invention relates to an endoscope used by inserting it into a human body, and an endoscope system including the endoscope.

2. Description of Related Art

Endoscopes are known as a means to observe organization and to carry out direct treatments by being inserted into a human body. A soft endoscope insertion section, inserted into the human body, is disposed on a tip of the endoscope main body gripped by the operator of the endoscope. Here, some conventional endoscopes have a detachable endoscope main body and a detachable endoscope insertion section (see, for example, Japanese Unexamined Patent Application, First Publication No. 2000-14626). The endoscope disclosed by Japanese Unexamined Patent Application, First Publication No. 2000-14626 is provided with a positioning mechanism for positioning an operation section, i.e., the endoscope main body and a soft section (i.e., the endoscope insertion section). A die (i.e., a positioning mechanism for determining an original point of a driving shaft) is freely disposed rotatively near the soft section. The operation section is provided an origin pin (i.e., a positioning mechanism compressed to a driving shaft by a spring) and a reference hole serving as an origin, to which the origin pin can be inserted, is formed on the driving shaft. When the positioning mechanism is used, after the origins are determined with respect to the operation section and the soft section respectively, the soft section is connected to the operation section. In addition, a connector to be connected with the optical fiber is disposed in a section where the operation section is attached to the insertion section. The structure of the connector is configured so that automatic positioning is carried out by inserting a pin disposed on the insertion section into a groove disposed on the operation section.

SUMMARY OF THE INVENTION

It is an object of the present invention to attach the endoscope insertion section to the endoscope main body and detach them easily and reliably, and in particular, to reduce loss of the transmitted light beam caused by the attachment and the detachment.

A first aspect of the present invention is an endoscope which includes: an endoscope insertion section; an endoscope main body assembled with the endoscope insertion section detachably; and an optical connector for connecting light guides for introducing light emission where each light guide is inserted into both the endoscope insertion section and the endoscope main body. In this aspect of the present invention, the endoscope insertion section and the endoscope main body are configured to be detachable from each other, and the optical connector is formed by a first connector section, supported in the endoscope main body, for fixing an end section of the light guide inserted into the endoscope main body; and a second connector section, supported by the endoscope insertion section and engageable with the first connector section, for fixing an end of the light guide inserted into the endoscope insertion section. In addition, one of the first connector section and the second connector section is supported movably with respect to the other one of the connectors.

In the event that there is a position shift between both connector sections in this endoscope, one of the connector sections moves so as to compensate the position shift and accepts the other one of the connectors. By doing this, the light guide in the endoscope main body is connected to the light guide in the endoscope insertion section without the position shift.

In a second aspect of the present invention, one of the freely movable connector sections is supported movably in a direction approximately orthogonal with respect to the insertion direction of the other connector section.

In the event that there is a position shift between the connector sections in a direction orthogonal with respect to the insertion direction in this endoscope, one of the connector sections moves in accordance with the position shift; therefore, the position shift is corrected.

In a third aspect of the present invention, one of the freely movable connector sections is supported movably with respect to the insertion direction of the other connector section.

In the event that there is a position shift between the connector sections in the insertion direction in this endoscope, one of the connector sections moves in accordance with the position shift; therefore, the position shift is corrected.

In a fourth aspect of the present invention, the endoscope further includes an attachment-detachment-detecting section for detecting the attachment or detachment state of the endoscope insertion section and the endoscope main body. In this aspect of the present invention, the attachment-detachment-detecting section is disposed so that the detecting action is conducted during detaching the endoscope insertion section from the position where the first connector section and the second connector section engage with each other to the position where the first connector section and the second connector section are fully separate.

Since both connector sections must be fully separate in order to fully separate the endoscope main body and the endoscope insertion section, the attachment-detachment-detecting section operates when a movement amount of the endoscope insertion section is a predetermined length shorter than the engagement of the connector sections (i.e., the attachment-detachment-detecting section emits a signal indicating, for example, that the endoscope insertion section has been detached).

A fifth aspect of the present invention is an endoscope system which includes the fourth aspect of the endoscope and an endoscope-controlling section connected to the endoscope so that the endoscope-controlling section is provided with an light-source-controlling section for interrupting the light emission when the attachment-detachment-detecting section detects that the connection at the connector sections is released.

The endoscope system includes the endoscope and the endoscope-controlling section so that the light emission from the end section of the light guide in the endoscope main body is interrupted because, for example, the light-source-controlling section stops supplying electric power to the light-emitting light source based on the output from the attachment-detachment-detecting section.

According to the present invention, since the optical connector for connecting the light guides inserted in the endoscope main body and the endoscope insertion section are respectively formed by the first connector section and the second connector section, and one of the connector sections is supported to be freely movable with respect to the other one of the connector sections, even if there is a position shift between the connector sections when the endoscope main body is attached to the endoscope insertion section, the light guides can be connected with each other and the position shift can be corrected by moving one of the connector sections. Therefore, it is possible to connect the light guides reliably and thus, it is possible to reduce loss in the transmitted light without using expensive parts for the optical connector.

Also, providing the attachment-detachment-detecting section enables a user to observe that the endoscope insertion section has been detached before both light guides are fully separated. If the attachment-detachment-detecting section and the endoscope-controlling section are configured to operate sequentially, it is possible to prevent light emission while the endoscope insertion section is detached.

DETAILED DESCRIPTION OF THE INVENTION

The best mode of the present invention will be explained with reference to drawings.

Figure 1:
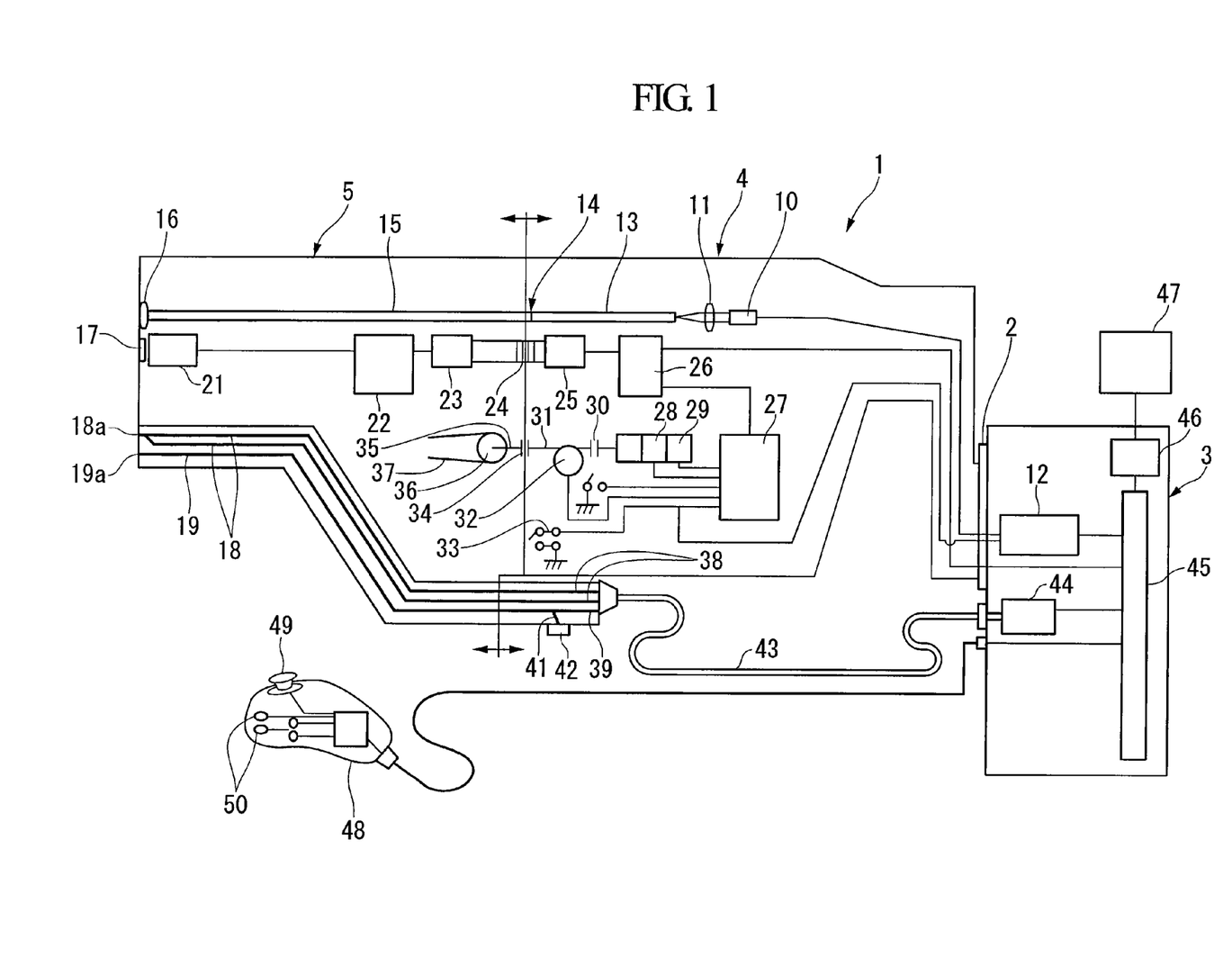
FIG. 1 is a general view of a structure of the endoscope system according to embodiments of the present invention.

As shown in FIG. 1, an endoscope system includes an endoscope 1 and an endoscope-controlling section 3 connected to the endoscope 1 by a connector 2 so that the endoscope 1 is provided to an endoscope main body 4 used outside of a human body; and an endoscope insertion section 5 configured to be attachable and detachable with respect to the endoscope main body 4 by a detachable mechanism so as to be inserted into the human body.

A lamp 10 (i.e., a light-emitting light source) and a light-condensing lens 11 for condensing the light emission emitted from the lamp 10 are disposed in the endoscope main body 4 of the endoscope 1. The lamp 10 is connected to a lamp-controlling section 12 (i.e., a light-source-controlling section) in the endoscope-controlling section 3. Also, an end section of the first light guide 13 formed by optical fibers is disposed in the vicinity of a focal position of the light-condensing lens 11. An optical connector 14 is disposed on the other end section of the first light guide 13 so that the end section of the second light guide 15 in the vicinity of the endoscope insertion section 5 is connected through this optical connector 14. The other end section of the second light guide 15 is disposed in the vicinity of the tip of the endoscope insertion section 5. A light-emitting lens 16 is disposed between the tip of the endoscope insertion section 5 and the tip of the second light guide 15.

In addition to the light-emitting lens 16, provided onto a tip of the tip end section of the endoscope insertion section 5 are: a CCD (charge-couple-device) 17, (i.e., an image-capturing section); an aperture section 18a of a duct 18 used for feeding air or water (A/W); and an aperture section 19a of a duct 19 for air intake.

The CCD 17 is connected to an I/O (input/output) unit 22 via a CCD driver 21. The I/O circuit 22 is configured to emit signals via a two-way-communication circuit 23. The two-way-communication circuit 23 is connected to a two-way-communication circuit 25 disposed in the endoscope main body 4 via an electric connector 24. A bending-motor-controlling device 27 and a lamp-controlling section 12 of the endoscope-controlling section 3 are connected to the two-way-communication circuit 25 via an I/O circuit 26.

A bending motor 28 for driving and bending a tip end section of the endoscope insertion section 5 and an encoder 29 for detecting a rotational position of the bending motor 28 are connected to the bending-motor-controlling device 27. Furthermore, connected to the bending-motor-controlling device 27 are a rotational-position-detecting section 32 for detecting a rotational position of a gear array 31 connected to the bending motor 28 via a clutch 30; and a attachment-detachment-detecting switch 33 disposed in the endoscope main body 4 for detecting the attachment-detachment-state of the endoscope insertion section 5. The gear array 31 is configured so as to be capable of transmitting rotation to a gear array 35 in the vicinity of the endoscope insertion section 5 via a connector 34. A pulley 36 is attached to this gear array 35 around which an angle wire 37 is wound for bending the tip end section of the endoscope insertion section 5.

The ducts 18, 19 in the endoscope insertion section 5 are connected to the ducts 38, 39 in the endoscope main body 4 via a base end section of the endoscope insertion section 5, and aperture sections 18a, 19a are formed at the ends of the ducts 38, 39 on the distal side of the endoscope main body 4. A side hole 41, into which a treatment instruments not shown in the drawings can be inserted, is formed on the air-intake-duct 39 so that this side hole 41 can be closed by a forceps stopple 42. Furthermore, a tube 43 is connected to the ducts 38, 39 so as to cover the aperture sections 18a, 19a (i.e., the tube 43) is connected to an intake-exhaust-controlling section 44 in the endoscope-controlling section 3.

The endoscope-controlling section 3 includes an intake-exhaust-controlling section 44; a lamp-controlling section 12; a comprehensive controlling section 45 for controlling the endoscope-controlling section 3 and the intake-exhaust-controlling section 44; and an image-processing section 46 for processing signals captured by the CCD 17. The image-processing section 46, connected to a monitor 47, is configured to display the image inside of the human body. Also, a remote-control-operation section 48 is attached to the comprehensive controlling section 45 via a cable. Provided onto the remote-control-operation section 48 are a joy stick 49 for bending the tip end section of the endoscope insertion section 5 and a plurality of switches 50 for controlling various functions (e.g., taking in air, exhausting air, and feeding fluid).

Here, the configuration of the optical connector 14 and the attachment-detachment-detecting switch 33 will be explained in detail with reference to FIG. 2. Here, FIG. 2 shows a separated state of the endoscope main body 4 and the endoscope insertion section 5.

Figure 2:
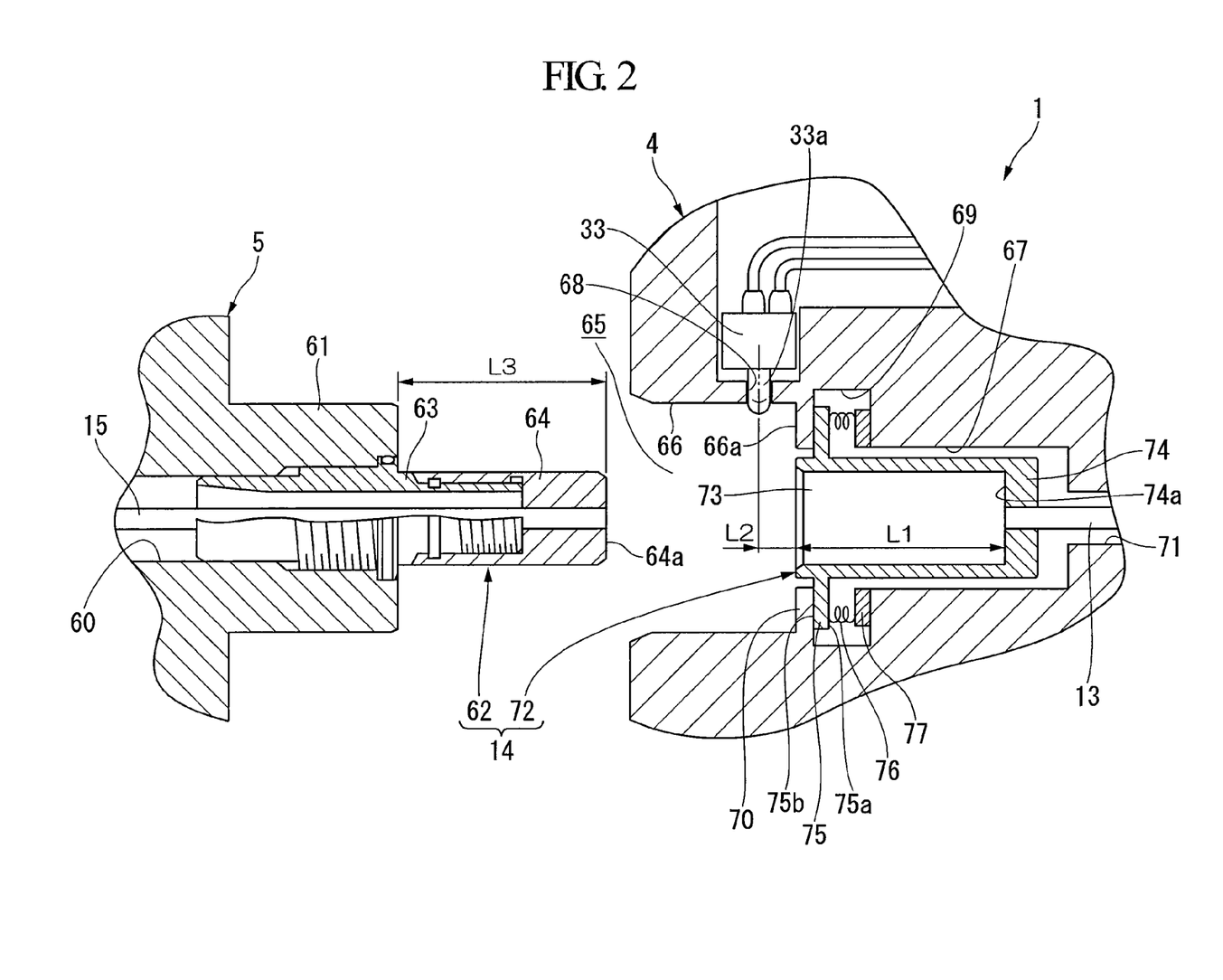
FIG. 2 shows a configuration of the optical connector in a state where the endoscope main body and the endoscope insertion section are separate.

As shown in FIG. 2, a through hole 60 into which a second light guide 15 is inserted is formed in the endoscope insertion section 5. A circular-projecting section 61 is formed on a base end portion of the endoscope insertion section 5 by protruding a marginal section of the through hole 60 protruding in a longitudinal direction so that a plug section 62 (i.e., a second connector section of the optical connector 14) is attached into the circular-projecting section 61. A cap 64 is fixed on a tip of the cylindrical main body section 63 of the plug section 62. The second light guide 15 is inserted in parallel in a center of the cap 64 so that an end surface of the end section of the second light guide 15 and a tip end surface 64a of the cap 64 coincide approximately with each other. The base end portion of the main body section 63 of the plug section 62 is screwed into the circular-projecting section 61, and in addition, the plug section 62 is retained by an O-ring in a liquid-tight manner.

On the other hand, a connector-receiving section 65 (i.e., a recessive section having a corresponding shape to the circular-projecting section 61) is formed on the tip end section of the endoscope main body 4. The connector-receiving section 65, having in general a columnar shape having a step formed by a terminal end surface 66a, is formed by a circular receiver 66 for receiving the circular-projecting section 61; and a housing section 67 formed by further recessing a central portion of the terminal end surface 66a of the receiver 66 for receiving the circular-projecting section. A side hole 68 is formed on a peripheral wall of the receiver 66 for receiving the circular-projecting section so that a detector 33a of the attachment-detachment-detecting switch 33 is inserted into this side hole 68 so as to be capable of freely protruding and recessing there with respect to the surface of the peripheral wall. Also, a circular groove 69 having an enlarged diameter with respect to the surface of the housing section 67 is formed in the vicinity of the step section there so that the groove 69 and the stepped section form a circular stopper section 70. An end of the housing section 67 communicates with an insertion hole 71 in which the first light guide 13 is inserted, and a socket section 72 (i.e., a first connector section for supporting the other end of the first light guide 13) is movably supported in the housing section 67.

The cylindrical socket section 72 is configured to take a cylindrical shape having a bottom section and has an aperture section 73 in the vicinity of the receiver 66 for receiving the circular-projecting section; and the other end section of the first light guide 13 is inserted and fixed in the socket section 72 so that the surface of the other end section and an inner surface 74a of the bottom section 74 coincide with each other. The diameter of the inner surface of the aperture section 73 increases in a tapered shape toward the end surface. Furthermore, a flange section 75 outwardly expands from an outer periphery in the vicinity of the aperture section 73 in a radial direction and is inserted into the circular groove 69 in the vicinity of the housing section 67. The outer diameter of the flange section 75 is configured to be smaller than the diameter of the groove 69. An end of a flexible member 76 (e.g., a compression coil spring) is fixed on a reference end surface 75a of the flange section 75. The other end of the flexible member 76 fitted to a ring plate 77 which is movably inserted into the groove 69. Since the flexible member 76 imparts a force to separate the flange section 75 from the ring plate 77 under a normal conditions, a tip end surface 75b of the flange section 75 makes contact to the stopper section 70. In this state, the end surface of the aperture section 73 and the terminal end surface 66a of the receiver 66 for receiving the circular-projecting section approximately coincide with each other.

The outer diameter of the socket section 72 is smaller than the diameter of the housing section 67, and the inner diameter of the socket section 72 is approximately the same as the outer diameter of the plug section 62. The socket section 72 is configured to have a length shorter than the length of the housing section 67. Length L1 between the bottom section 74 of the socket section 72 and the end surface of the aperture section 73 is approximately the same as a projection length L3 of the plug section 62. Furthermore, a length L2 between the end surface of aperture section 73 and the detector 33a of an attachment-detachment-detecting switch 33 is shorter than the projection length L3 of the plug section 62.

Operations in the present embodiment will be explained as follows.

In order to attach the endoscope insertion section 5 to the endoscope main body 4 that are in the separated state as shown in FIG. 2, the endoscope insertion section 5 is inserted so that the positions of the connectors 14, 24, and 34 shown in FIG. 1 coincide with each other. The plug section 62 as shown in FIG. 2 is inserted into the socket section 72 through the receiver 66 for receiving the circular-projecting section; the tip end surface 64a of the plug section 62 makes contact to an inner surface 74a of bottom section 74 of socket section 72; thus, end surfaces of the light guides 13, 15 make close contact with each other.

Here, in the event that the position of the plug section 62 and the position of the socket section 72 are shifted slightly in a direction orthogonal with respect to the insertion direction, the position shift is corrected by moving the flange section 75 so as to slide on a stopper section 70 by the socket section 72; thus the plug section 62 is accepted. In this state, the plug section 62 is forwarded and engaged in the housing section 67 smoothly due to the tapered shape formed in the aperture section 73 of the socket section 72. Also, since the diameter of the first light guide 13 is smaller than a diameter of the insertion hole 71, if the plug section 62 moves, no load is imposed onto the first light guide 13.

Furthermore, if the position of the plug section 62 is shifted from the position of the socket section 72 slightly in the insertion direction, the flange section 75 compresses the flexible member 76 while the socket section 72 accepts the plug section 62; as a result, the whole part of the socket section 72 retracts along the groove 69 so as to accept and engage with the plug section 62.

Figure 3:
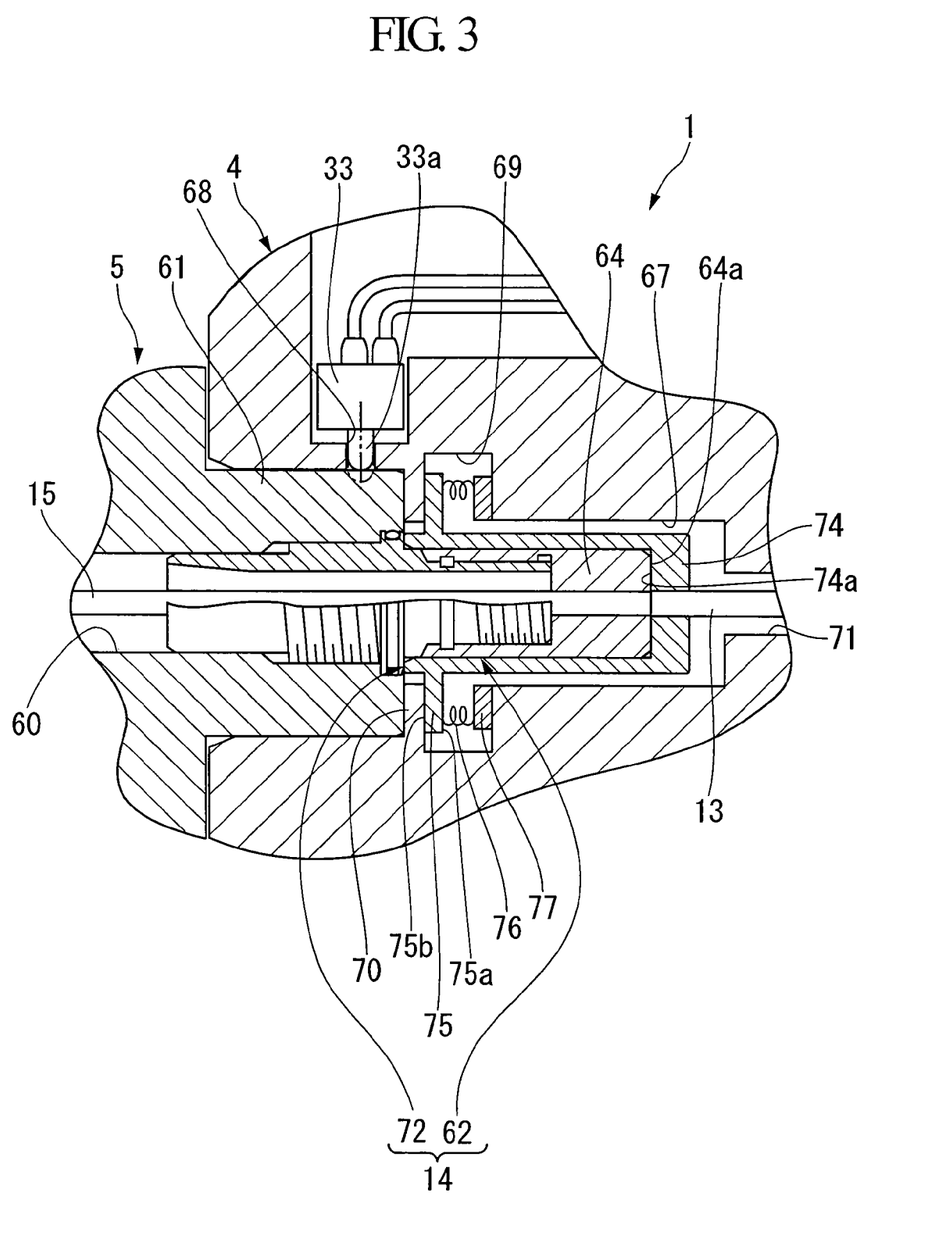
FIG. 3 shows the optical connectors in a state where the endoscope insertion section is attached.

Along with the engagement of the plug section 62 into the socket section 72, a circular-projecting section 61 engages with the receiver 66. In this state, as shown in FIG. 3, the detector 33a of attachment-detachment-detecting switch 33 projecting from the side surface of the receiver 66 recesses by the circular-projecting section 61 compressing back the detector 33a. By doing this, contact points in the attachment-detachment-detecting switch 33 close; thus, a signal is output. This signal is output to the bending-motor-controlling device 27 and to the lamp-controlling section 12 shown in FIG. 1. The bending-motor-controlling device 27 having received the signal permits the drive of the bending motor 28, and after that, it is possible to bend the tip end section of endoscope insertion section 5 corresponding to the joy stick 49 of the remote-control-operation section 48 moved by the operator. Also, since the lamp-controlling section 12 outputs the signal permitting to operate the lamp 10, it is possible to emit light from the tip of endoscope insertion section 5.

Figure 4:
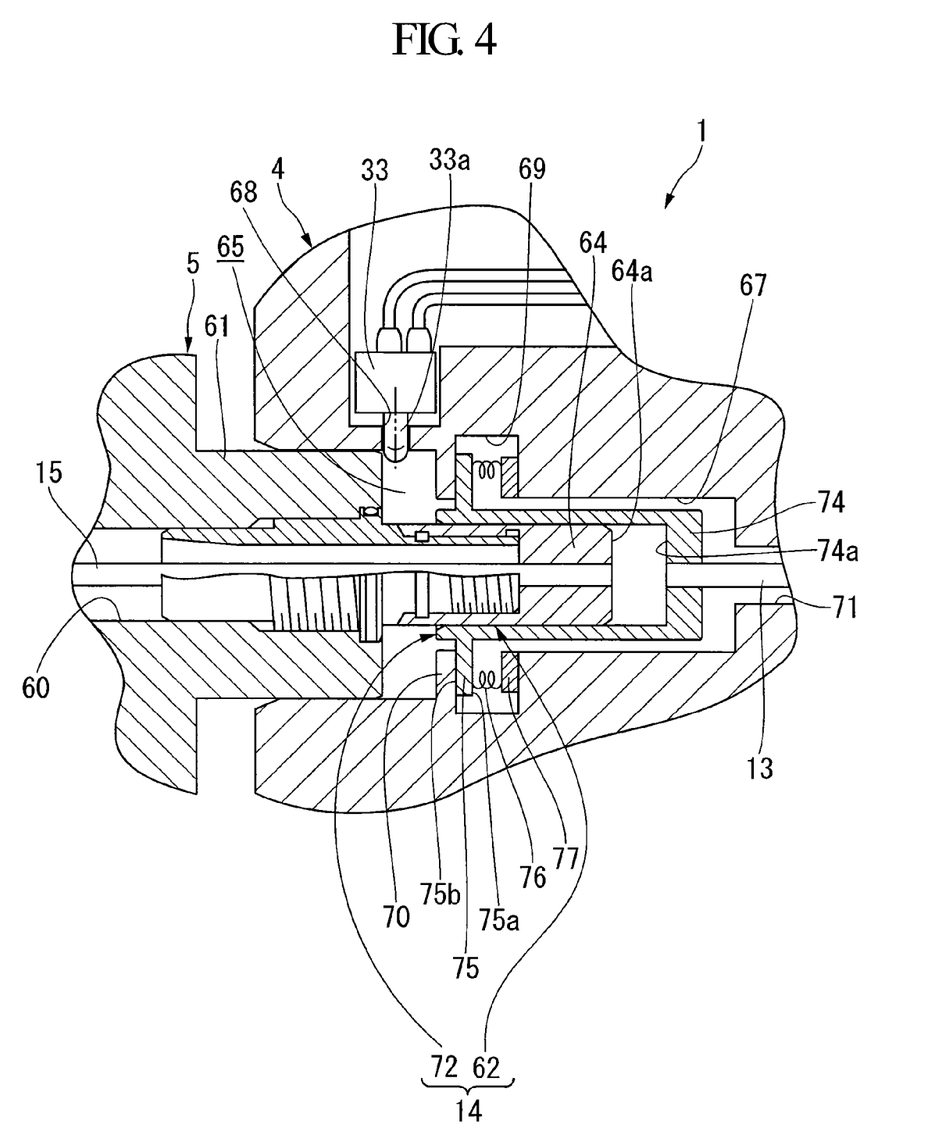
FIG. 4 shows processes for detaching the endoscope insertion section.

Also, the detachable mechanism not shown in the drawing is detached so as to separate the endoscope insertion section 5 from the endoscope main body 4. In this state, as shown in FIG. 4, the circular-projecting section 61 is separate from the terminal end surface 66a of receiver 66 for receiving the circular-projecting section before the plug section 62 is fully retracted from the socket section 72; thus, the circular-projecting section 61 is retracted farther from the position where the side hole 68 is formed. In this state, the movement amount of the endoscope insertion section 5 is equivalent to a distance longer than the length L2 and shorter than a distance of the projection length L3 shown in FIG. 2. In this state, the detector 33a of attachment-detachment-detecting switch 33 protrudes again and the contact points open; thus the signal output is interrupted. The bending-motor-controlling device 27 shown in FIG. 1 inhibits the drive of the bending motor 28, and after that, the endoscope insertion section 5 cannot be bent. Also, the lamp-controlling section 12 interrupts the supply of electric power to the lamp 10 (i.e., turns off the lamp 10 if it has been turned on).

In the present embodiment, since the socket section 72 in the vicinity of the endoscope main body 4 is supported movably with respect to the insertion direction and to the direction orthogonal to the insertion direction, the socket section 72 can be engaged with the plug section 62 while correcting such a position shift even if the position of endoscope insertion section 5 is shifted from the position of endoscope main body 4. Therefore, it is possible to attach the endoscope insertion section 5. Thus, operability is enhanced. Also, since the end surfaces of the light guides 13, 15 can be contacted closely (i.e., without the position shift because the socket section 72 moves), it is possible to reduce transmission loss in the optical connector 14.

Furthermore, since the attachment-detachment-detecting switch 33 is configured to interrupt the signal output before the plug section 62 is fully separated from the socket section 72, it is possible to detect that the endoscope insertion section 5 has been separated before the endoscope insertion section 5 is fully separated from the endoscope main body 4. Also, since it is possible to interrupt the drive (e.g., the bending of the endoscope insertion section 5) and to turn off the lamp 10 in sequence of the attachment-detachment-detecting switch 33, the rotation of gear array 31 and light emission are restricted under the condition that the endoscope insertion section 5 is not attached.

It should be noted that the present invention is not limited to the above embodiment, i.e., the present invention can be applied to various aspects.

For example, it is possible to detect the attachment-detachment-state of the endoscope insertion section 5 more reliably by disposing a plurality of attachment-detachment-detecting switches 33.

The socket section 72 may be supported movably only in a direction orthogonal with respect to the insertion direction. In this condition, the length of groove 69 is configured so that the groove 69 makes contact slidably with the flange section 75.

The socket section 72 may be fixed in the endoscope main body 4, and the plug section 62 may be supported movably in the endoscope insertion section 5. The mechanism for supporting the plug section 62 (the same as that shown in FIG. 2) can be adapted. Also, the plug section 62 may be disposed in the endoscope main body 4 and the socket section 72 may be disposed in the endoscope insertion section 5 so that either one of them is supported movably.

The light source is not limited to the lamp 10 (i.e., the light source may be capable of oscillating a laser beam, for example, a laser diode).

What is claimed is:

1. An endoscope comprising:
an endoscope insertion section; an endoscope main body assembled with the endoscope insertion section detachably; and
an optical connector for connecting a first light guide and a second light guide for introducing light emission, the first light guide being inserted into the endoscope main body, and the second light guide being inserted into the endoscope insertion section, wherein
the endoscope insertion section and the endoscope main body are configured to be detachable from each other,
the optical connector is formed by a first connector section, supported in the endoscope main body, and fixed to an end section of the first light guide inserted into the endoscope main body; and a second connector section, supported by the endoscope insertion section and engageable with the first connector section, and fixed to an end of the second light guide inserted into the endoscope insertion section, and
one of the first connector section and the second connector section is supported movably in the endoscope main body or in the endoscope insertion section, so as to enable it to be axially aligned with respect to the other connector section,
wherein one of the first connector section and the second connector section is supported movably in a direction approximately orthogonal with respect to the insertion direction of the other connector section,
the first light guide and the second light guide are formed by optical fibers, and
the first light guide and the second light guide are connected to each other when the first connector section and the second connector section are connected, and
further comprising an attachment-detachment-detecting section for detecting a state of attachment or detachment of the endoscope insertion section and the endoscope main body, wherein
the attachment-detachment-detecting section is disposed so that a detecting movement is conducted during detaching the endoscope insertion section from a position where the first connector section and the second connector section engage with each other to a position where the first connector section and the second connector section are fully separated, wherein
the first connector section is supported movably in the endoscope main body and formed in a cylindrical socket shape which has a bottom section and an aperture section,
the second connector section is supported in the endoscope insertion section and formed in a cylindrical shape which can be inserted in the aperture section of the first connector section,
the endoscope insertion section is provided with a circular-projecting section formed in a cylindrical shape which has a lager diameter than a diameter of the second connector section,
the endoscope main body is provided with a connector-receiving section which can receive circular-projecting section,
the aperture section of the first connector section is located in the bottom section and facing toward the endoscope insertion section,
an end face of the circular-projecting portion is facing toward the endoscope main body and the second connector section is supported so as to protrude from the end face of the circular-projecting portion,
the attachment-detachment-detecting section is provided with a detector which is capable of freely protruding and recessing from a side wall of the connector-receiving section in a radial direction of the circular-projecting portion, and
a length between the aperture section of the first connector section and the detector in the insertion direction of the second connecter section is shorter than a projection length of the second connector section projecting from the circular-projecting section.

2. An endoscope according to claim 1, wherein one of the first connector section and the second connector section is supported movably with respect to the insertion direction of the other connector section.

3. An endoscope system comprising:
the endoscope according to claim 1, and an endoscope-controlling section connected to the endoscope, wherein the endoscope-controlling section is provided with a light-source-controlling section for interrupting the light emission when the attachment-detachment-detecting section detects that a connection at the connector sections is released.

4. An endoscope according to claim 1, wherein the first connector section is supported movably in the endoscope main body.

5. An endoscope according to claim 1, wherein the second connector section is supported movably in the endoscope insertion section.

6. An endoscope according to claim 1, wherein the first connector section has a cylindrical socket having a bottom.

* * * * *